United States Patent [19]

Ng

[11] Patent Number: 5,069,665
[45] Date of Patent: Dec. 3, 1991

[54] FLUID ASPIRATION NEEDLE

[76] Inventor: Raymond C. Ng, 1737 Oak Grove, San Marino, Calif. 91108

[21] Appl. No.: 546,896

[22] Filed: Jul. 2, 1990

[51] Int. Cl.$^5$ .............................................. A61M 31/00
[52] U.S. Cl. ..................................... 604/51; 604/187; 604/117; 128/765
[58] Field of Search ................ 604/117, 164, 167, 169, 604/170, 51, 53, 93, 181, 187, 272; 128/763, 765

[56] References Cited

U.S. PATENT DOCUMENTS

| | | | |
|---|---|---|---|
| 1,215,512 | 2/1917 | Fetzer | 604/272 |
| 2,032,723 | 3/1936 | Schweser | 604/183 |
| 2,091,438 | 8/1937 | Epstein | 604/117 |
| 2,338,800 | 1/1944 | Burke | 604/117 |
| 2,922,420 | 1/1960 | Cheng | 604/272 |
| 2,952,256 | 9/1960 | Meader et al. | 604/272 |
| 3,630,198 | 12/1971 | Henkin | 604/170 |
| 3,703,899 | 11/1972 | Calinog | 604/170 |
| 3,896,810 | 7/1975 | Akiyama | 604/117 |
| 4,020,835 | 5/1977 | Nordstrom et al. | 604/168 |
| 4,096,860 | 6/1978 | McLaughlin | 604/167 |
| 4,490,139 | 12/1984 | Huizenga et al. | 604/57 |
| 4,531,935 | 7/1985 | Berryessa | 604/53 |
| 4,531,937 | 7/1985 | Yates | 604/53 |
| 4,565,545 | 1/1986 | Suzuki | 604/164 |
| 4,721,506 | 1/1988 | Teves | 604/51 |
| 4,760,847 | 8/1988 | Vaillancourt | 606/185 |
| 4,799,494 | 1/1989 | Wang | 604/51 |
| 4,810,244 | 3/1989 | Allen | 604/164 |
| 4,834,722 | 5/1989 | Zenz | 604/272 |
| 4,850,975 | 7/1989 | Furukawa | 604/170 |

FOREIGN PATENT DOCUMENTS

| | | | |
|---|---|---|---|
| 1092011 | 4/1955 | France | 604/170 |
| 238082 | 2/1969 | U.S.S.R. | 604/117 |
| 8909025 | 10/1989 | World Int. Prop. O. | 128/763 |

Primary Examiner—Gene Mancene
Assistant Examiner—Michael Lynch
Attorney, Agent, or Firm—William W. Haefliger

[57] ABSTRACT

A fluid aspiration needle assembly comprising a linearly elongated, tubular needle having a first end to be positioned at or proximate a patient's body, and an opposite end portion; a hub integral with the opposite end portion of the needle and providing a reservoir, the hub having a first duct in linear communication with the needle via the reservoir, and there being a second duct in communication with the reservoir and branching relatively away from the first duct, the second duct connected to the hub; the first duct, reservoir and needle being in linear alignment to receive an elongated stylet having a sharp end, and manipulable to cause the sharp end to penetrate the patient's body, and to be withdrawn so that body fluid can pass through the needle and enter the reservoir; and flexible, coupler tubing operatively connected to the second duct for passing fluid between the reservoir and a syringe operatively connected to the reservoir via the flexible tubing, whereby the syringe may be bodily manipulated in force-transmitting relation isolation relative to the needle.

8 Claims, 2 Drawing Sheets

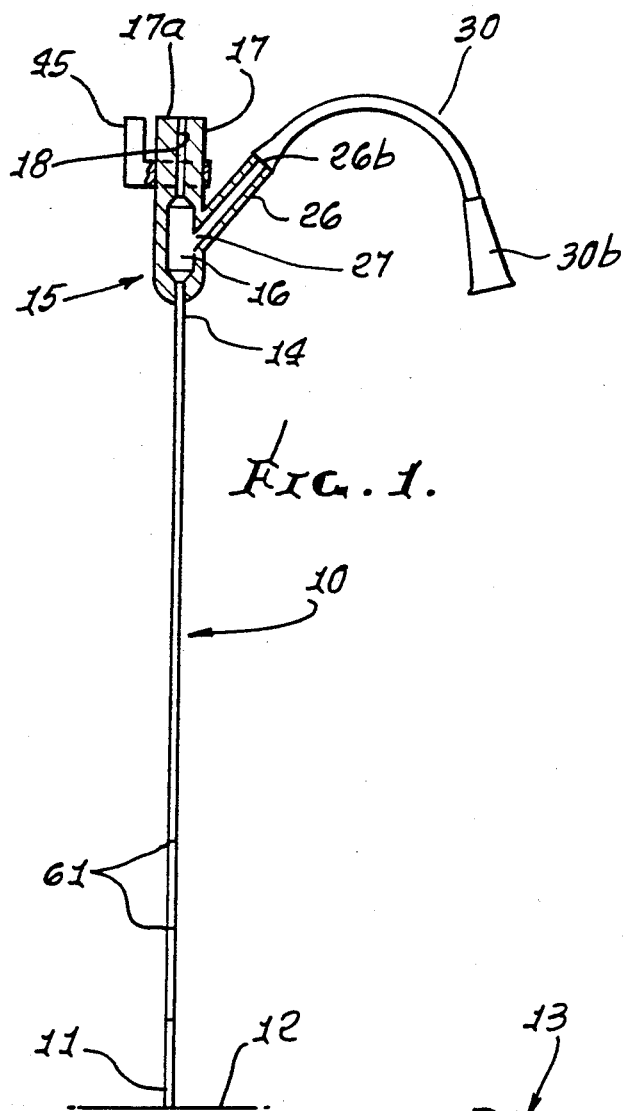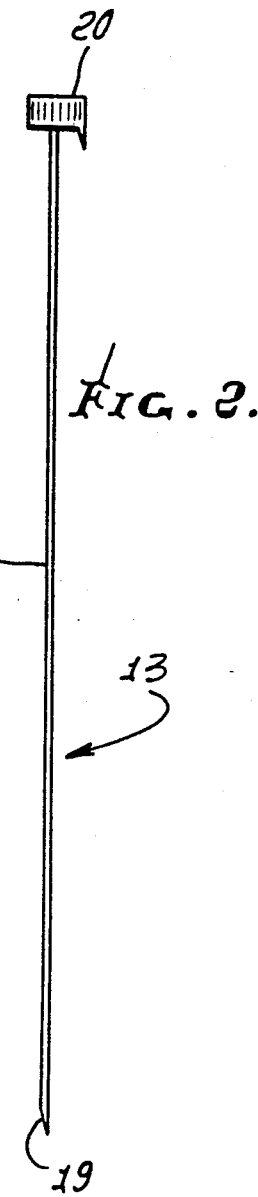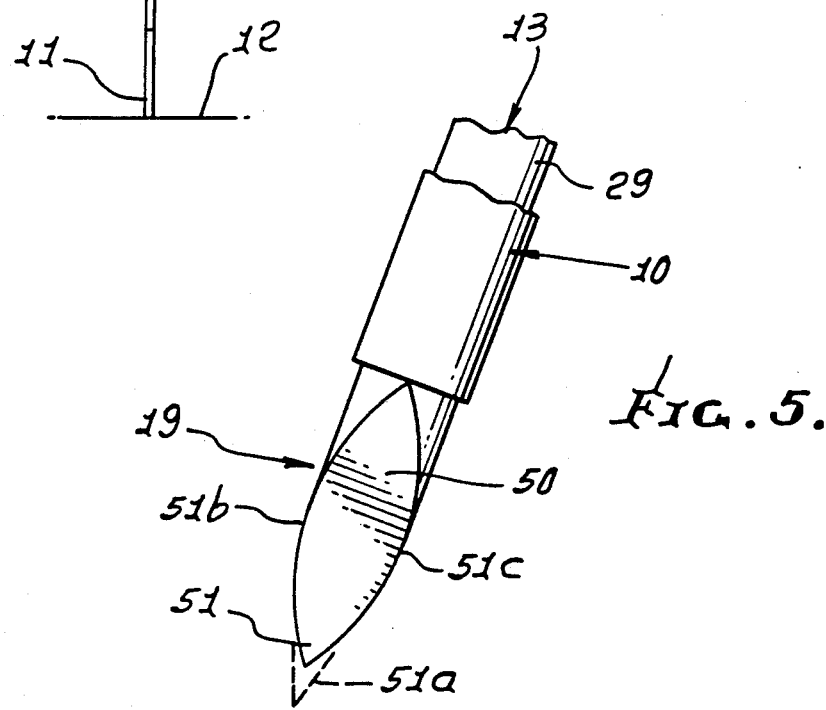

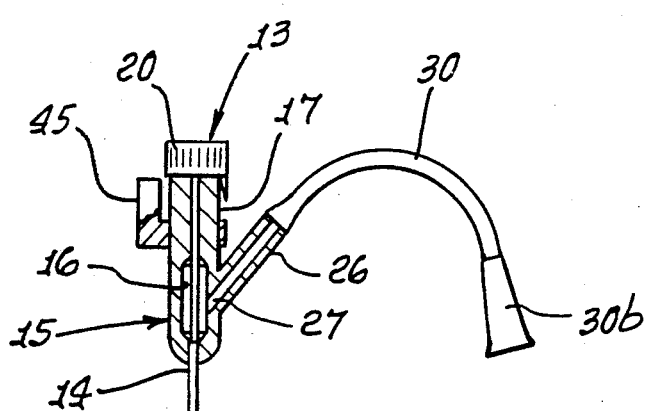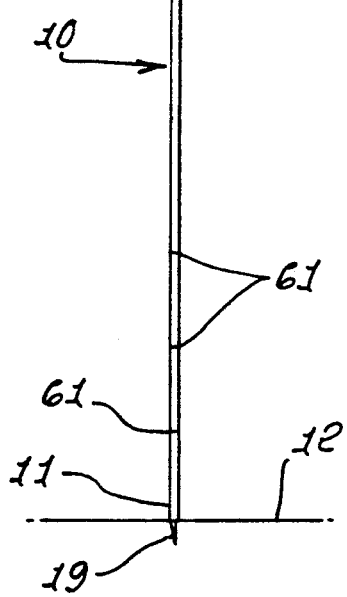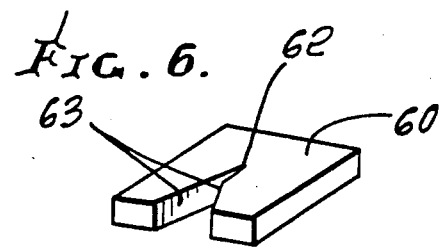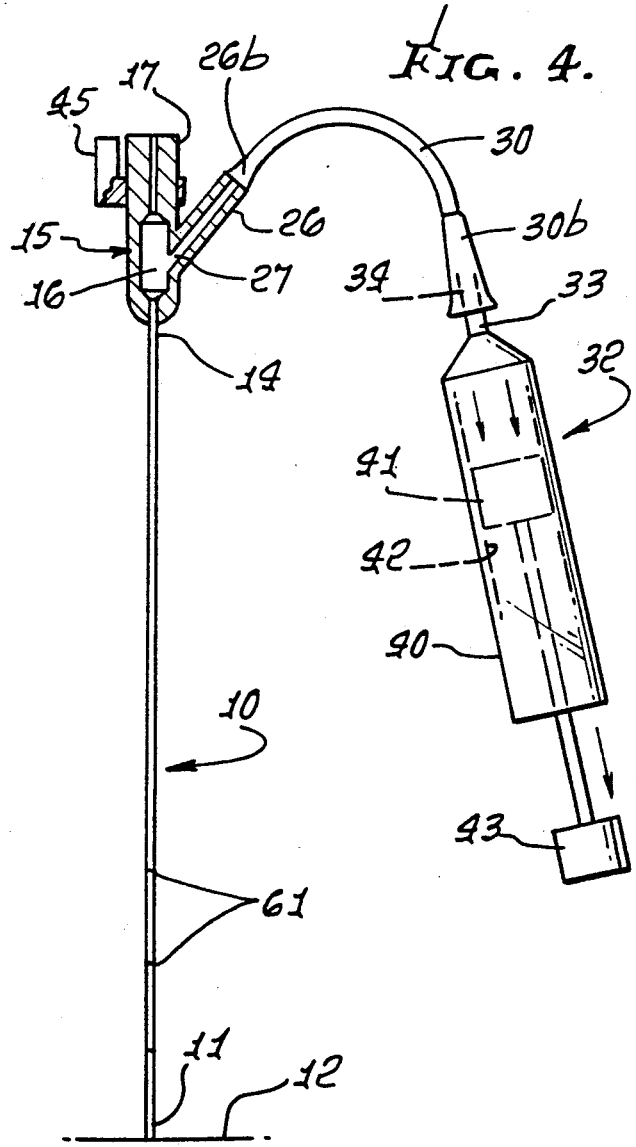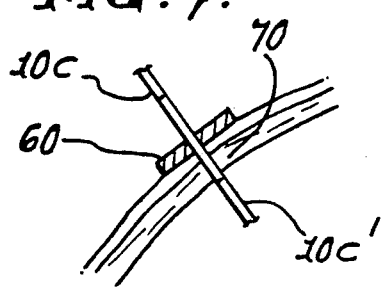

FLUID ASPIRATION NEEDLE

BACKGROUND OF THE INVENTION

This invention relates generally to body fluid aspiration, and more particularly to improvements in needles and associated equipment used for such aspiration.

Needles are commonly inserted into a patient's body for fluid aspiration as by use of a syringe connected with the needle structure. Manipulation of the syringe to effect aspiration must be carefully carried out in order to minimize force transmission to the needle, as for example axially (which could be dangerous if the needle is inadvertently pushed further into the body) or laterally (which tends to enlarge the needle entry wound in the body). There is need for a means to prevent these occurrences, while allowing free manual manipulation of the syringe. There is also need for improvements in structure associated with the needle, and a stylet in the needle, to enhance their effectiveness in use.

SUMMARY OF THE INVENTION

It is a major object of the invention to provide means meeting the above needs. Basically, the invention is embodied in a body fluid aspiration needle assembly that includes:

a) a linearly elongated, tubular needle having a first end to be positioned at or proximate a patient's body, and an opposite end portion, b) a hub integral with the opposite end portion of the needle and providing a reservoir, the hub having a first duct in linear communication with the needle via the reservoir, and there being a second duct in communication with the reservoir and branching relatively away from the first duct, the second duct connected to the hub, c) the first duct, reservoir and needle being in linear alignment to receive an elongated stylet having a sharp end, and manipulable to cause the sharp end to penetrate the patient's body, and to be withdrawn so that body fluid can pass through the needle and enter the reservoir, d) and flexible, coupler tubing operatively connected to the second duct for passing fluid between the reservoir and a syringe operatively connected to the reservoir via the flexible tubing, whereby the syringe may be bodily manipulated in force-transmitting relative isolation relative to the needle.

As will be seen, the hub and ducts are typically integral, with the ducts extending in Y-shaped relative configuration; and a stopper is typically associated with the first duct and manipulable to close the first duct after withdrawal of the stylet from the needle.

It is another object of the invention to provide an improved stylet inserted into and extending within the needle, the stylet having a first end portion protruding from the needle to penetrate the patient's body. As will be seen, the stylet is cylindrical and longitudinally and axially elongated, and the first end portion thereof defines a side flat that tapers from one side of the end portion toward the other side thereof. The flat typically terminates at a tapered tip and the flat has edges extending toward the tip, at least one of the tip and edges being dulled to reduce the sharpness thereof.

Yet another object is to provide a marker body removably and frictionally attached to the needle, and adjustable along the needle length to a selected position to indicate depth of needle penetration into the patient's body. As will be seen, the marker body advantageously comprises a flat plate easily adjusted manually to flatly fit against the patient's body, and it has an opening therethrough to pass the needle, and also having a through fissure extending from the plate edge to the opening to pass the needle sidewardly relative to the marker body and into the opening, for use on the needle.

These and other objects and advantages of the invention, as well as the details of an illustrative embodiment, will be more fully understood from the following specification and drawings, in which:

DRAWING DESCRIPTION

FIG. 1 is a side elevation showing a needle and associated hub and ducts, and flexible branch tubing;

FIG. 2 is an elevation showing a stylet to be received in the needle;

FIG. 3 shows the stylet inserted into the needle to produce a body puncture;

FIG. 4 is a view like FIG. 1 showing a syringe attached to the flexible branch tubing;

FIG. 5 is an enlarged fragmentary side view of a terminal portion of the stylet;

FIG. 6 is a perspective view of a flat marker plate; and

FIG. 7 is a section showing use of the marker plate on a needle.

DETAILED DESCRIPTION

In the drawings, fluid aspiration needle 10 is linearly elongated and has a lower, i.e., first, end 11 to be positioned at or proximate a patient's body 12, to enter a wound or puncture produced by tip 51 of a stylet 13. The opposite end portion 14 of the needle is integral with a hub 15, which is enlarged and tubular, to form a reservoir 16. The hub includes an integral first duct 17 in linear communication with the needle, via the reservoir, so that the stylet can be passed through the bore 18 of the duct 17, then through the reservoir, and into and through the needle to puncture the body as seen in FIG. 3.

The stylet 13 includes an elongated, narrow, cylindrical shaft 29, sharpened at its lower end portion 19. A flange 20 at the upper end of the stylet is manually manipulable to insert the stylet in the needle hub 15, and it is downwardly engageable with the upper end 17a of the first duct to limit downward displacement of the stylet sharpened lower end relative to the needle. The lower end 11 of the needle is blunt, to rest against the body surface 12 during stylet manipulation, but the needle is thin-walled to permit its travel into the wound produced by the stylet, for fluid aspiration.

As seen in the drawings, a second duct 26 is also in communication with the reservoir, at its side (see location 27); and the second duct is connected with the side of the hub to branch away from the hub, in Y-shaped relation with the first duct. Both ducts are typically formed of rigid plastic material, as is the hub; but they could consist of other material, such as metal. Flexible tubing 30 is operatively connected to the end 26b of the second duct for passing body fluid collecting in the reservoir to a syringe 32 seen in FIG. 4. While that syringe has a tube 33 suitably removably connected at 34 to a flared wall portion 30b of the tubing 30, manual manipulation and displacement of the syringe during its use creates force that is not transmitted to the needle, due to flexing of the coupler tubing 30. This feature is important, since endwise or lateral displacement of the needle, while it is in the wound or puncture formed by the stylet, could be dangerous, as for example to a fetus during amniocentesis. The syringe includes the usual cylinder 40, plunger 41 in chamber 42, and handle 43.

In use, the stylet is withdrawn from the wound and may be withdrawn from the needle during insertion of the needle into the wound, and to desired depth. The first duct 17 is closed, after removal of the stylet, as by rotation of a stopper 45 to close the bore of 17. The needle is then pushed into the body, via the needle. The syringe is then attached to 30b and used to draw liquid from the body via reservoir 16. The syringe is then detached, and the needle withdrawn.

FIG. 5 shows the cylindrical stylet lower end as sharpened due to forming of a side flat 50 angled to taper from one side of the stylet toward the other, and endwise toward tip 51. The sharp, tapered tip 51 may be slightly dulled or blunted, as from a more sharp condition, indicated by broken lines 51a, formed when flat 50 is ground. The sharp, lateral edges 51b and 51c of the flat may also be slightly dubbed for safety.

FIGS. 6 and 7 show use of a flat plate marker 60, adjustably positioned on the needle shank 10c and held in position by friction at selected "depth" (needle penetration) position, indicated by notches or other indicators 61 on the shank. The flat plate has an undersized opening 62 to pass the needle, but also to grip it, frictionally. A side fissure 63 in the plate is tapered as shown, and allows relative movement of the needle shank sidewardly into through opening 62, the shank tending to slightly spread the opening to provide friction.

FIG. 7 shows the needle shank extent 10c', below the marker, penetrating the body at 70. The plate flatly engages the body outer skin surface to limit needle penetration.

The needle assembly, as described, may be suitably disposed of after use.

I claim:

1. In a fluid aspiration needle assembly, the combination comprising:
   a) a linearly elongated tubular needle having a first end to be positioned at or proximate a patient's body, and an opposite end portion,
   b) an enlarged hub integral with said opposite end portion of the needle and providing a reservoir, the hub having a first duct in linear communication with the needle via said reservoir, and there being a second duct in communication with the reservoir and branching relatively away from the first duct, the second duct connected to the hub,
   c) the first duct, reservoir and needle being in linear alignment to receive an elongated stylet having a sharp end, and manipulable to cause said sharp end to penetrate the patient's body, and to be withdrawn so that body fluid can pass through the needle and enter the reservoir,
   d) and flexible, coupler tubing operatively connected to said second duct for passing fluid between the reservoir and a syringe operatively connected to said reservoir via said flexible tubing, whereby the syringe may be bodily manipulated in force-transmitting relation isolation relative to the needle, and including said syringe removably connected to said flexible tubing, remote from the reservoir,
   e) there being a stopper at said hub first duct and operable to close said first duct, after withdrawal of the stylet from the needle.

2. The combination of claim 1 wherein said hub, and said first and second ducts are integral, the ducts having Y-shaped relative configuration.

3. The combination of claim 1 including said stylet inserted into and extending within the needle, the stylet having a first end portion protruding from the needle to penetrate the patient's body, said stopper being open.

4. The combination of claim 3 wherein the stylet is cylindrical and longitudinally and axially elongated, and said first end portion thereof defines a side flat that tapers from one side of said end portion toward the other side thereof.

5. The combination of claim 4 wherein said flat terminates at a tapered tip and the fact has edges extending toward said tip, at least one of said tip and edges being dulled to reduce the sharpness thereof.

6. The combination of claim 1 including a marker body removably and frictionally attached to the needle, and adjustable along the needle length to a selected position to indicate depth of needle penetration into the patient's body.

7. The combination of claim 1 wherein said hub is enlarged relative to the needle.

8. In a fluid aspiration needle assembly, the combination comprising:
   a) a linearly elongated, tubular needle having a first end to be positioned at or proximate a patient's body, and an opposite end portion,
   b) a hub integral with said opposite end portion of the needle and providing a reservoir, the hub having a first duct in linear communication with the needle via said reservoir, and there being a second duct in communication with the reservoir and branching relatively away from the first duct, the second duct connected to the hub,
   c) the first duct, reservoir and needle being in linear alignment to receive an elongated stylet having a sharp end, and manipulable to cause said sharp end to penetrate the patient's body, and to be withdrawn so that body fluid can pass through the needle and enter the reservoir,
   d) and flexible, coupler tubing operatively connected to said second duct for passing fluid between the reservoir and a syringe operatively connected to said reservoir via said flexible tubing, whereby the syringe may be bodily manipulated in force-transmitting relation isolation relative to the needle,
   e) and a marker body removably and frictionally attached to the needle, and adjustable along the needle length to a selected position to indicate depth of needle penetration into the patient's body, said marker body being a plate having an opening therethrough to pass the needle, and also having a through fissure extending from the plate edge to said opening to pass the needle sidewardly relative to the marker body and into said opening, for use on the needle.

* * * * *